(12) United States Patent
Hauger et al.

(10) Patent No.: US 10,939,816 B2
(45) Date of Patent: Mar. 9, 2021

(54) MICROSCOPE

(71) Applicant: Carl Zeiss Meditec AG, Jena (DE)

(72) Inventors: Christoph Hauger, Aalen (DE);
Thorsten Tritschler, Aalen (DE);
Manfred Dick, Gefell (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/165,750

(22) Filed: Oct. 19, 2018

(65) Prior Publication Data

US 2019/0117061 A1 Apr. 25, 2019

(30) Foreign Application Priority Data

Oct. 20, 2017 (DE) .......................... 102017124545.6

(51) Int. Cl.
*A61B 3/103* (2006.01)
*A61B 3/10* (2006.01)
(Continued)

(52) U.S. Cl.
CPC ............ *A61B 3/1035* (2013.01); *A61B 3/102* (2013.01); *A61B 3/1015* (2013.01); *A61B 3/13* (2013.01); *A61B 18/20* (2013.01); *A61F 9/008* (2013.01); *A61F 9/00821* (2013.01); *A61F 9/00825* (2013.01); *G02B 21/00* (2013.01); *G02B 21/0012* (2013.01); *G02B 21/082* (2013.01);
(Continued)

(58) Field of Classification Search
CPC ......... A61B 3/10; A61B 3/1005; A61B 3/101; A61B 3/1015; A61B 3/102; A61B 3/103; A61B 3/1035; A61B 3/13; G02B 21/0012; G02B 21/0082; A61F 2009/00848; A61F 2009/00851; A61F 2009/0087
USPC .......................................... 351/205–208, 246
See application file for complete search history.

(56) References Cited

U.S. PATENT DOCUMENTS 4,691,997 A 9/1987 Muchel
7,488,070 B2 2/2009 Hauger et al.
(Continued)

FOREIGN PATENT DOCUMENTS

DE 103 60 570 B4 7/2005
DE 10 2008 047 400 A1 4/2010
(Continued)

OTHER PUBLICATIONS

English translation of German Office Action for Application No. 10 2017 124 545.6, dated Aug. 6, 2018 (9 pgs).
(Continued)

*Primary Examiner* — Travis S Fissel
(74) *Attorney, Agent, or Firm* — Patterson Thuente Pedersen, P.A.

(57) ABSTRACT

A microscope, comprising an observation beam path that renders an eye to be examined observable, a wavefront measuring device for measuring the refraction of the eye to be examined, an OCT device comprising an OCT illumination beam path, by means of which OCT illumination radiation can be focused as an OCT spot into the eye to be examined, and a control unit that is supplied with at least one measurement value of the wave front measuring device, is provided, wherein the control unit sets the beam diameter and/or the beam shape of the OCT spot on the basis of the at least one supplied measurement value.

20 Claims, 1 Drawing Sheet

(51) Int. Cl.
*A61B 3/13* (2006.01)
*G02B 21/00* (2006.01)
*A61F 9/008* (2006.01)
*A61B 18/20* (2006.01)
*G02B 21/08* (2006.01)

(52) U.S. Cl.
CPC .............. *A61B 2018/20359* (2017.05); *A61F 2009/0087* (2013.01); *A61F 2009/00848* (2013.01); *A61F 2009/00851* (2013.01); *A61F 2009/00863* (2013.01)

(56) References Cited

U.S. PATENT DOCUMENTS

| | | | |
|---|---|---|---|
| 7,845,798 B2 | 12/2010 | Kuebler et al. | |
| 8,459,795 B2 | 6/2013 | Seesselberg et al. | |
| 9,560,963 B2 | 2/2017 | Buckland et al. | |
| 2003/0007124 A1* | 1/2003 | Levine | A61F 9/008 351/206 |
| 2003/0139736 A1 | 7/2003 | Sander | |
| 2007/0013918 A1 | 1/2007 | Hauger et al. | |
| 2008/0117503 A1 | 5/2008 | Reimer et al. | |
| 2008/0125763 A1 | 5/2008 | Arnoldussen et al. | |
| 2009/0257065 A1 | 10/2009 | Hauger et al. | |
| 2010/0321675 A1 | 12/2010 | Huang et al. | |
| 2010/0324542 A1 | 12/2010 | Kurtz | |
| 2012/0069303 A1 | 3/2012 | Seesselberg et al. | |
| 2012/0082410 A1 | 4/2012 | Peng et al. | |
| 2012/0147460 A1 | 6/2012 | Kübler et al. | |
| 2013/0021576 A1* | 1/2013 | Saito | A61B 3/12 351/206 |
| 2013/0131652 A1 | 5/2013 | Dick et al. | |
| 2013/0211391 A1 | 8/2013 | BenYakar et al. | |
| 2014/0107634 A1* | 4/2014 | Vogler | A61F 9/008 606/6 |
| 2015/0002812 A1* | 1/2015 | Yoshihara | G06T 7/0016 351/206 |
| 2015/0031993 A1 | 1/2015 | Buckland et al. | |
| 2015/0077705 A1 | 3/2015 | Artsyukhovich et al. | |
| 2015/0216408 A1* | 8/2015 | Brown | A61B 3/1015 351/206 |
| 2016/0360961 A1 | 12/2016 | Buckland et al. | |
| 2016/0365697 A1 | 12/2016 | Hori et al. | |
| 2017/0189228 A1 | 7/2017 | Yang et al. | |
| 2018/0064338 A1* | 3/2018 | Neal | A61F 9/00804 |

FOREIGN PATENT DOCUMENTS

| | | | |
|---|---|---|---|
| DE | 10 2008 063 644 A1 | 7/2010 | |
| DE | 10 2010 024 606 A1 | 12/2011 | |
| EP | 3 005 938 A2 | 4/2016 | |
| EP | 3005938 A2 * | 4/2016 | A61B 3/102 |
| WO | WO 2008/061034 A1 | 5/2008 | |
| WO | WO 210/031540 A2 | 3/2010 | |
| WO | WO 2011/091283 A1 | 7/2011 | |
| WO | WO 2014/074636 A1 | 5/2014 | |
| WO | WO 2015/017375 A2 | 2/2015 | |
| WO | WO 2015/042305 A1 | 3/2015 | |
| WO | WO 2015/130651 A1 | 9/2015 | |

OTHER PUBLICATIONS

Benabid et al., "Fiber for fiber lasers: Kagome PC fiber goes to extremes for ultrashort-pulse Lasers," Sep. 8, 2014 (8 pgs).
German Office Action for Application No. 10 2017 124 545.6, dated Aug. 6, 2018 (10 pgs).
"Lensx Laser," www.myalcon.com/products/surgical/lensx-laser/index.shtml (2 pgs).
"Liquid Crystal Switchable Mirror," KentOptronics product information sheet (2 pgs).
Kozak et al., "Modern retinal laser therapy," *Saudi Journal of Ophthalmology* (2015) 29, pp. 137-146 (10 pgs).
Ober et al., "Retinal Lasers: Past, Present, and Future," *Retinal Physician*, Jan. 1, 2009 (6 pgs).
"Visumax," www.zeiss.com/meditec/us/products/ophthalmologyoptometry/cornea-refractive/laser-treatment/femtosecond-lasersolutions/visumax.html (1 pg).

* cited by examiner

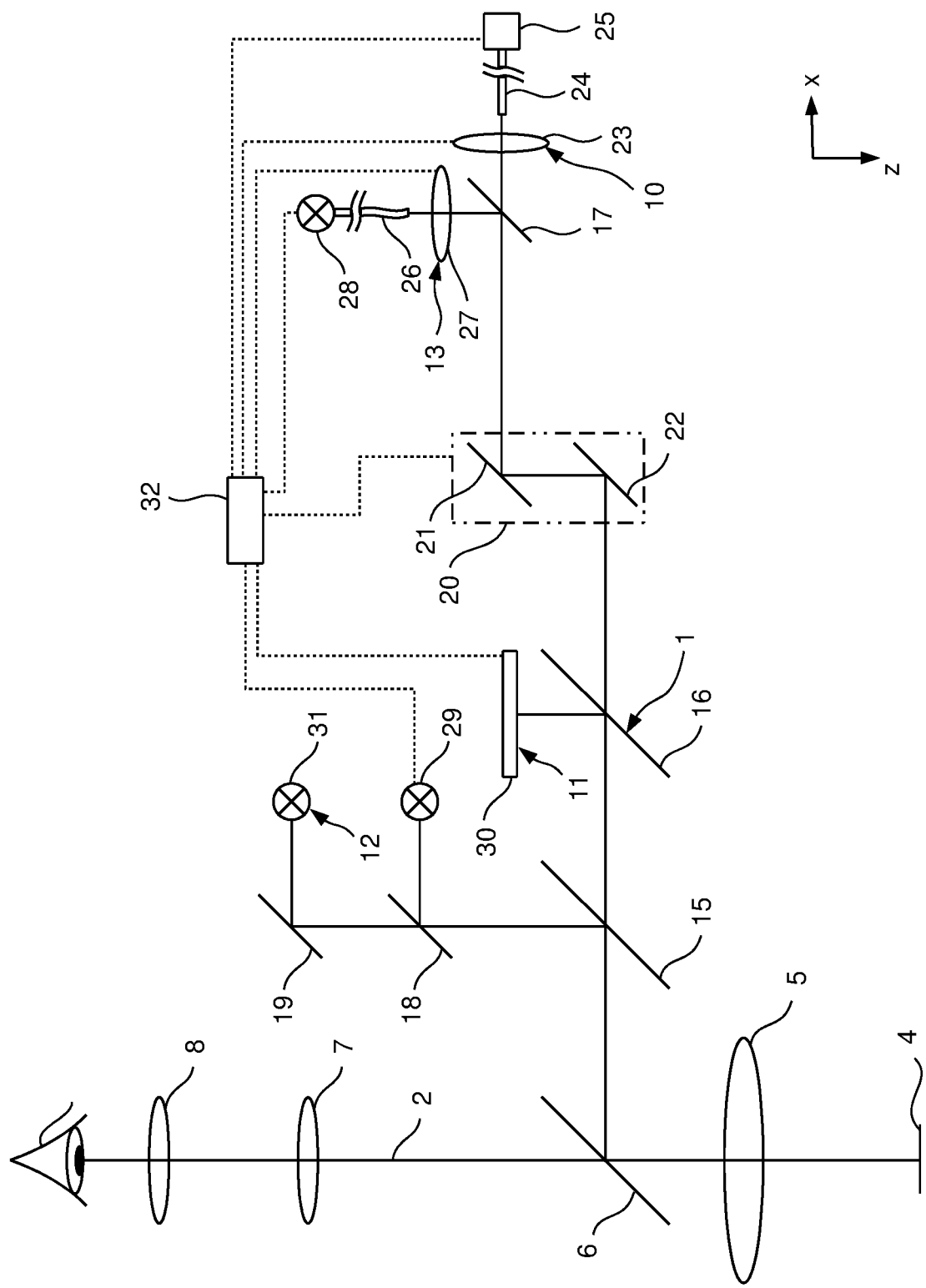

MICROSCOPE

RELATED APPLICATIONS

The present application claims the priority of German patent application 10 2017 124 545.6, filed on 20 Oct. 2017, with the entire content of said application herewith being incorporated herein by reference.

FIELD OF THE INVENTION

The present invention relates to a microscope. In particular, it relates to a surgical microscope, which can be used in eye surgery for interventions in the aqueous and/or vitreous humor of the eye.

BACKGROUND

Cataracts and glaucoma treatments are common interventions in the aqueous humor. Interventions on the retina, such as membrane peeling and macular hole interventions, can be carried out in the vitreous humor.

In these interventions (on the retina, in particular), treatment lasers (which may also be referred to as therapeutic lasers) are used for photocoagulation. In addition to these lasers with a thermal effect, ultrashort pulse lasers with pulse lengths in the fs-range have furthermore been clinically introduced in recent years for interventions in the eye. In particular, these ultrashort pulse lasers are used for refractive corrections in the cornea or for assisting a cataract operation in the lens. Additionally, the use for vitreous humor and retinal surgery has already been described.

Further, the wavefront measurement has been introduced in recent years in the field of eye surgery, for the purposes of intraoperative measurement of the refraction of the eye, for example, as has optical coherence tomography (OCT) for making retinal structures visible during operation, for example.

SUMMARY OF THE INVENTION

Proceeding herefrom, it is therefore an object of the invention to provide a microscope which uses the described, known technologies for a microscope with improved properties.

The invention is defined in Claim 1. Advantageous developments are specified in the dependent claims.

The microscope according to the invention can comprise an observation beam path that renders an eye to be examined observable (preferably in magnified fashion), a wavefront measuring device for measuring the refraction of the eye to be examined, an OCT device comprising an OCT illumination beam path, by means of which OCT illumination radiation can be focused as an OCT spot into the eye to be examined, and a control unit that is supplied with at least one measurement value of the wave front measuring device. The control unit can set the beam diameter and/or the beam shape of the OCT spot on the basis of the at least one supplied measurement value.

Hence, the measurement of the wavefront measuring device is advantageously used to be able to set properties of the OCT spot in individual fashion to the eye currently under examination. Hence, an extremely high accuracy is achieved since the defocusing and/or deformation of the OCT spot caused by the individual eye to be examined can be compensated well.

The wavefront measuring device can measure the spherical aberration of the eye to be examined. Further, the wavefront measuring device can measure the astigmatism of the eye to be examined. This can be carried out so quickly with the desired accuracy that this measurement can be evaluated in real time and can be used for setting the beam diameter and/or the beam shape of the OCT spot.

In particular, the control unit can actuate the OCT device in such a way that a defocusing and/or deformation are impressed on the OCT illumination radiation, said defocusing and/or deformation being opposite to the defocusing and/or deformation caused by the eye to be examined.

The OCT device can comprise a collimation optical unit for collimating the OCT illumination radiation, wherein the control unit actuates the collimation optical unit for the purposes of setting the beam diameter and/or the beam shape of the OCT spot.

In particular, the collimation optical unit can comprise an axially displaceable lens. For the purposes of setting the beam diameter of the OCT spot, the control unit can set the axial position of the lens.

Further, the collimation optical unit can comprise a liquid lens, which is actuated accordingly by the control unit for the purposes of setting the beam diameter and/or the beam shape of the OCT spot.

Moreover, the collimation optical unit can comprise an adaptive mirror, the control unit actuating said adaptive mirror for the purposes of setting the beam diameter and/or the beam shape of the OCT spot.

The observation beam path may comprise a main objective. Further, the main objective can be part of the OCT illumination beam path and/or part of a detection beam path of the wavefront measuring device. Since the OCT measurement beam path runs counter to the OCT illumination beam path, the main objective also can be part of the OCT measurement beam path. Furthermore, the main objective can be part of the illumination beam path of the wavefront measuring device.

The microscope can comprise an illumination device. The illumination device comprises an illumination beam path, which may comprise the main objective. The illumination device can be embodied as coaxial illumination and, in particular, as stereo coaxial illumination (SCI). In particular, it can be embodied in the same way as the illumination device 120 in EP 1 918 756 B1. Here, reference is made, in particular, to FIGS. 1 to 5 with the associated description.

The microscope can be embodied as a stereo microscope with two observation beam paths (e.g., optical observation beam paths). Both observation beam paths may contain the main objective as an objective. Further, the microscope can comprise an eyepiece in the observation beam path (or in each observation beam path). In particular, the microscope is embodied as a surgical microscope.

Further, the microscope can comprise a treatment laser device, by means of which pulsed laser radiation (e.g., ps- or fs-pulses) can be provided for the eye to be examined and optionally treated. The treatment laser device may comprise a corresponding treatment laser (e.g., fs/ps treatment laser). For the purposes of attaching the treatment laser or transmitting the laser radiation from the treatment laser to the microscope, provision can be made of a flexible fiber that, in particular, is embodied as a hollow-core fiber or photonic crystal fiber. The high pulse peak powers of the laser pulses emitted by the treatment laser can be transmitted without problems using such a fiber. Using the flexible fiber, the (pulsed) treatment laser radiation can be guided to a free beam path of the microscope.

The OCT device can comprise a deflection unit (or scanning unit) in order to move the OCT illumination radiation in the eye. In particular, the microscope can be embodied in such a way that the laser radiation of the treatment laser is deflected and moved by way of the same scanning unit.

The microscope can comprise a treatment laser device having a treatment laser beam path rendering it possible to focus the treatment laser radiation as a treatment laser spot into the eye to be examined and optionally treated. The control unit can set the beam diameter and/or the beam shape of the treatment laser spot on the basis of the at least one supplied measurement value. Here, the wavefront measuring device can measure the spherical aberration and/or the astigmatism of the eye to be treated.

The control unit can actuate the treatment laser device in such a way that a defocusing and/or deformation are impressed on the treatment laser radiation, said defocusing and/or deformation being opposite to the defocusing and/or deformation caused by the eye to be treated.

The treatment laser device can comprise a collimation optical unit for collimating the treatment laser radiation, wherein the control unit actuates the collimation optical unit for the purposes of setting the beam diameter and/or the beam shape of the treatment laser spot. Here, the collimation optical unit of the treatment laser device can comprise an axially displaceable lens, the axial position of which is set by means of the control unit for the purposes of setting the beam diameter of the treatment laser spot.

Further, the collimation optical unit of the treatment laser device can comprise a liquid lens, which is actuated by the control unit for the purposes of setting the beam diameter and/or the beam shape of the treatment laser spot.

The collimation optical unit of the treatment laser device can comprise an adaptive mirror, the control unit actuating said adaptive mirror for the purposes of setting the beam diameter and/or the beam shape of the treatment laser spot.

The main objective of the observation beam path can also be part of the treatment laser beam path.

It goes without saying that the aforementioned features and those yet to be explained below can be used not only in the combinations specified but also in other combinations or on their own, without departing from the scope of the present invention.

BRIEF DESCRIPTION OF THE DRAWINGS

Below, the invention will still be explained in more detail on the basis of exemplary embodiments, with reference being made to the attached FIG. 1, which is a schematic illustration of an exemplary embodiment of the microscope according to the invention and which likewise discloses features that are essential to the invention. These exemplary embodiments serve merely for illustration and should not be interpreted as restrictive. By way of example, a description of an exemplary embodiment with a multiplicity of elements or components should not be interpreted to the effect that all these elements or components are necessary for implementation purposes. Rather, other exemplary embodiments also may contain alternative elements and components, fewer elements or components or additional elements or components. Elements or components of different exemplary embodiments can be combined with one another, unless indicated otherwise. Modifications and developments which are described for one of the exemplary embodiments may also be applicable to other exemplary embodiments.

DETAILED DESCRIPTION

In the exemplary embodiment shown in FIG. 1, the microscope 1 according to the invention is embodied as a stereo surgical microscope 1 having two optical observation beam paths, of which only one observation beam path 2 is illustrated schematically in FIG. 1. The beam path 2 extends from an object 4 to be observed through a main objective 5, and then through a first beam splitter 6, a zoom optical unit 7 and an eyepiece 8 such that an observer can perceive, in magnified fashion and by way of their eye A, the object 4 to be observed.

The microscope 1 further comprises an OCT (optical coherence tomography) device 10, a wavefront measuring device 11, an illumination device 12 and a treatment laser device 13.

As described in detail below, the beam paths of these devices 10-13 are overlaid and deflected towards the objective 4 by means of the first beam splitter 6. To this end, provision is made of a second, third, fourth and fifth beam splitter 15, 16, 17, 18, a deflection mirror 19, and a scanning unit 20 with a first and second deflecting mirror 21, 22. The OCT device 10 comprises a first collimator optical unit 23, a first light guide 24 and an OCT module 25. During operation, the OCT module 25 produces the necessary coherent illumination radiation, which may have a wavelength of 1060 nm, for example. The coherent illumination radiation is guided through the first light guide 24 and collimated by means of the first collimator optical unit 23. By means of the first and second deflecting mirror 21, 22, the scanning unit 20 implements the desired deflection in the x-direction and y-direction such that coherent illumination radiation from the scanner unit 20 is steered to the objective 4 via the third, second and first beam splitter 16, 15, 6 and focused at the desired location in the object 4 by means of the objective 5 in order thereby to produce detection radiation, said radiation being guided to the OCT module counter to the coherent illumination radiation. In order to simplify the illustration, further optical imaging elements between the first collimator optical unit 23 and the objective 5 that are known to a person skilled in the art and required to realize the described focusing of the scanned coherent illumination radiation are not plotted.

The produced detection radiation passes along the illumination beam path of the OCT device 10 in the opposite direction and is guided to the OCT module 25 via the first light guide 24, the detection being implemented in said OCT module in a manner known per se.

The treatment laser device 13 comprises a second light guide 26 and a second collimator optical unit 27. The laser radiation of the illumination laser device 13 for treating the object 4, which may be an eye (in particular a human eye), for example, is coupled into the second light guide 26 and guided up to the second collimator optical unit 27, the latter collimating the laser radiation that is then steered via the fourth beam splitter 17 to the scanning unit 20 and then consequently passes along the same beam path as the illumination radiation of the OCT device 10. A treatment laser 28 emitting the laser radiation may be part of the treatment laser device 13. The treatment laser 28 emits pulsed laser radiation in the femtosecond or picosecond range, in particular, and can therefore be referred to as an fs-laser or as a ps-laser. The wavelength of the emitting laser radiation may lie in the infrared range, e.g., in the range of 800-900 nm or in the range of 1000-1100 nm, or else in the visible wavelength range. Here, typical wavelengths are 532, 561, 577, 660 or 670 nm.

The wavefront measuring device 11 comprises an illumination laser 29, which emits laser radiation with a wavelength from the range of 750-850 nm, for example, said laser radiation being steered towards the objective 5 by the fifth and second and also first beam splitter 18, 15, 6. Further, the wavefront measuring device 11 comprises a wavefront sensor 30 (e.g., a Shack-Hartmann camera 23) for detection purposes, wherein the radiation to be detected is steered towards the wavefront sensor 30 via the main objective 5 and the first, second and third beam splitter 6, 15 and 16.

The illumination device 12 comprises a light source 31, which emits illumination radiation in the range of 400-700 nm, said illumination radiation being steered towards the main objective 5 via the deflection mirror 19 and via the fifth, second and first beam splitter 18, 15, 6.

In order to simplify the illustration, further optical imaging elements of the wavefront measuring device 11 and of the illumination device 12, in addition to the main objective 5, are not illustrated, as these are known to a person skilled in the art.

Further, provision is made of a control unit 32, which is connected, inter alia, to the wavefront sensor 30, the scanning unit 20, the treatment laser 28, the OCT module 25 and the two collimator optical units 23 and 27 and which can control the microscope 1, as will still be described below.

In order to realize the described overlay of the beam paths of the devices 10-13, the first to fifth beam splitter 6, 15-18 are embodied as dichroic beam splitters. The reflection and transmission values for the beam splitters 6, 15-18 are specified as percentages in Tables 1 to 5 below. In the same way, values for the first and second deflecting mirror 21 and 22, and for the deflection mirror 19, are specified in Tables 6 and 7 below. Here, SCI represents the radiation of the light source 31, OCT represents the radiation of the OCT module, WFS represents the radiation of the illumination laser and LASER represents the radiation of the treatment laser 28.

TABLE 1

(first beam splitter 6; VIS = visible wavelength range; IR = infrared range):

|  | Reflection [in %] | Transmission [in %] |
|---|---|---|
| SCI | 30 | 70 |
| OCT | 100 | 0 |
| WFS | 100 | 0 |
| LASER | 30 (VIS)/100 (IR) | 70 (VIS)/0 (IR) |

TABLE 2

(second beam splitter 15):

|  | Reflection [in %] | Transmission [in %] |
|---|---|---|
| SCI | 50 | 50 |
| OCT | 0 | 100 |
| WFS | 50 | 50 |
| LASER | 50 | 50 |

TABLE 3

(third beam splitter 16):

|  | Reflection [in %] | Transmission [in %] |
|---|---|---|
| OCT | 0 | 100 |
| WFS | 100 | 0 |
| LASER | 0 | 100 |

TABLE 4

(fourth beam splitter 17):

|  | Reflection [in %] | Transmission [in %] |
|---|---|---|
| OCT | 0 | 100 |
| LASER | 100 | 0 |

TABLE 5

(fifth beam splitter 18):

|  | Reflection [in %] | Transmission [in %] |
|---|---|---|
| SCI | 0 | 100 |
| WFS | 100 | 0 |

TABLE 6

(first and second deflecting mirror 21, 22):

|  | Reflection [in %] | Transmission [in %] |
|---|---|---|
| OCT | 100 | 0 |
| LASER | 100 | 0 |

TABLE 7

(deflection mirror 19):

|  | Reflection [in %] | Transmission [in %] |
|---|---|---|
| SCI | 100 | 0 |

These specifications are based on the considerations set forth below. The OCT beam path has to be optimized in respect of illumination and the OCT detection has to be optimized in respect of transmission since a reduction in the image quality is unwanted. In respect of transmission, the wavefront beam path is not as critical as the OCT beam path. Therefore, the wavefront beam path is optimized in respect of detection since losses in the wavefront illumination can be compensated by way of a stronger illumination laser 29. In the case of the radiation of the treatment laser 28, losses at the first and second beam splitter 6, 15 have to be accepted. However, these can be compensated by means of a higher output power of the treatment laser 28. The same applies to the light source 31 of the illumination device 12. The second beam splitter 15 can be adapted to the respective light source in respect of the 50/50 values of reflection and transmission for the beam path of the illumination device 12, the beam path of the wavefront measuring device 11 and the beam path of the treatment laser device 13.

When applying the microscope 1 according to the invention in the field of eye treatment, the quality of the OCT image data depends on the lateral diameter of the illumination beam on the retina of the eye 4 to be recorded (and optionally treated). Likewise, the efficiency of the photocoagulation, the photodisruption and/or the photoablation depends on the diameter of the laser spot of the laser radiation of the treatment laser 28 on the fundus.

According to the invention, the refraction of the eye 4 is measured in the case of the microscope 1 by means of the wavefront measuring device 11. In parallel thereto or separately therefrom, the spot diameter of the laser radiation of the OCT module and/or the spot diameter of the laser radiation of the treatment laser 28 then can be set taking account of the measured refraction. Setting the spot diameter of the laser radiation of the OCT module 25 can be implemented by means of the first collimation optical unit 23. Setting the spot diameter of the laser radiation of the treatment laser 28 can be implemented by means of the second collimation optical unit 27. By way of example, this can be implemented by the axial displacement of a lens of the corresponding collimation optical unit 23, 27. It is also possible for the collimation optical unit 23, 27 to comprise an adaptive mirror and/or a liquid lens with an electrically variable focal length.

Particularly when measuring and/or treating the retina, the eye 4 can defocus and/or deform the laser spot of the laser radiation of the OCT module 25 and/or the laser spot of the laser radiation of the treatment laser 28 (such that said laser spot is no longer round, for example). The measurement by means of the wavefront measuring device 11 can be implemented quickly and with great accuracy. Then, as already described above, the measurement results can be used to implement defocusing by means of the corresponding collimation optical unit 23, 27, said defocusing being exactly opposite to the defocusing caused by the eye 4. Naturally, an opposite deformation of the laser spot can be implemented in the same way in order to compensate the deformation of the laser caused by the eye 4. What this advantageously achieves is that the laser spot of the laser radiation of the OCT module 25 and/or the laser spot of the treatment laser 28 is in focus and round in the eye 4 to be treated, for example on the retina.

Naturally, it is possible not only to minimize the laser spot of the laser radiation of the treatment laser 28; it is also possible to set it to any desired diameter. This may be advantageous, particularly in the case of photocoagulation and/or photodisruption.

The microscope 1 according to the invention consequently allows controlling or setting the diameter of the laser spot of the laser radiation of the OCT module 25 and/or the diameter of the laser spot of the laser radiation of the treatment laser 28 in a targeted manner in respect of diameter and/or form on the basis of the measurement by means of the wavefront measuring device 11.

Further, a treatment mode can be realized using the microscope 1 according to the invention, in which treatment mode B-scans and/or volume data (referred to as OCT data below) are captured by means of the OCT device 10. By way of example, the OCT data can contain blood vessels and other retina structures. These structures can be established by evaluating the OCT data. By way of example, the evaluation can be implemented in real-time (or online). Then, on the basis of this evaluation, the treatment laser 28 with scanning unit 20 can be actuated in such a way that the desired locations are coagulated in a targeted manner.

By way of example, this treatment mode can be realized as a sequential or parallel treatment mode. In the case of the sequential treatment mode, the OCT data are measured first and, on the basis thereon, the desired locations are coagulated or cut using laser radiation of the treatment laser 28. In the parallel treatment mode, OCT data are measured and evaluated permanently or continuously. Then, the treatment laser 28 is only activated at the times at which, by means of the scanning unit 20, the laser beam of the OCT module 25 and the laser beam of the treatment laser 28 pass over the desired locations.

Attaching the treatment laser 28 to the microscope 1, which may be embodied as a movable surgical microscope 1, is difficult since the second light guide 26 cannot be realized by a conventional quartz glass fiber. Thus, the high pulse peak power of the laser pulses emitted by the treatment laser 28 would lead to the destruction of the input coupling surface of the second light guide. Therefore, a photonic crystal fiber (which is also referred to as a microstructured hollow-core fiber) is used as a second light guide. By way of example, the hollow-core diameter can be approximately 40 µm, with use being made of a so-called "Kagome" structure (Benabid et al., Laser Focus World, volume 50, September 2014, "Fiber For Fiber Lasers: Kagome PC fiber goes to extremes for ultrashort-pulse lasers"). In the case of such a hollow-core fiber, the ultrashort pulse radiation of the treatment laser 28 can be input coupled with approximately <20 mrad half angle, for example. The transmission losses are very low (a few percent) using such a fiber and the beam quality at the end of the fiber 26 is virtually maintained with a beam quality parameter product of $M^2<1.3$. Furthermore, this flexible fiber 26 is able to transfer even relatively large powers of approximately 500 W without problems. Since a maximum of approximately 10 W is required in medicine and, in particular, when treating eyes, such a fiber is very well suited to attach the treatment laser 28 to the microscope 1. Furthermore, there are no noticeable dispersion effects in the case of photonic crystal fibers when compared to quartz glass fibers, said dispersion effects causing unwanted changes in respect of the temporal pulse shape. Consequently, the described hollow-core fiber is a flexible fiber that, in particular, is suitable for the transmission or the transfer of fs and ps laser pulses.

For the purposes of photodisruption in the rear eye portion, it is necessary to focus the ultrashort pulse laser radiation with a comparatively low aperture. Thus, fs laser pulses with pulse energies in the nJ and µJ range are usually focused at apertures of NA>0.8 in order to produce a plasma at the focal spot which brings about photodisruption and consequently the formation of small bubbles in the usually transparent tissue. These points of photodisruption can be placed next to one another by means of the scanning unit 20 such that the tissue can be perforated and/or cut as a result thereof. Even in the case of apertures NA>0.25, this is still carried out in the front eye portion. Self-focusing increasingly occurs with fs laser pulses in the case of scanned ultrashort pulse laser radiation with a numerical aperture of less than 0.25, said self-focusing bringing about laser beam filamentation and consequently a jitter in the focal position, and hence inaccurate cutting by way of photodisruption. Therefore, ps laser pulses (0.7-20 ps and, in particular, 1-3 ps), in particular, are provided according to the invention for positionally accurate cuts in the rear eye portion and in the case of apertures of less than 0.25, said ps laser pulses having pulse energies in the µJ range and being used repetitively in the kHz range. If the treatment laser 28 operates repetitively in the MHz range, it is also possible to use smaller pulse energies in the lower µJ range or nJ range.

Hence, the flexible attachment of the ultrashort pulse treatment laser 28 to the surgical microscope 1 according to the invention by means of the microstructured hollow-core fiber 26 while maintaining the pulse quality and beam quality, the transmission within the microscope 1 in the case of a comparatively large beam diameter without intermediate focal spots (in particular on optical surfaces in order to avoid laser damage) and, in particular, the use of ps laser pulses facilitates jitter-free focusing in the rear eye portion for the purposes of exactly guiding the cut on structures of the retina and the vitreous humor of the eye 4 to be treated.

In an alternative embodiment, the laser radiation of the treatment laser 28 and the laser radiation of the OCT module 25 can be guided in the same fiber 24 or 26, if this can be tolerated for wavelength reasons and in view of requirements on the beam profile of the laser radiations.

The invention claimed is:

1. A microscope, comprising:
   an observation beam path that renders an eye to be examined observable;
   a wavefront measuring device for measuring the refraction of the eye to be examined;
   an OCT device comprising an OCT illumination beam path, by application of which OCT illumination radiation can be focused as an OCT spot into the eye to be examined; and
   a control unit that is supplied with at least one measurement value of the wave front measuring device, wherein the control unit sets the beam diameter and/or the beam shape of the OCT spot on the basis of the at least one measurement value, wherein the control unit actuates the OCT device in such a way that a defocusing and/or deformation is applied to the OCT illumination radiation by application of an adjustable collimation optical unit, said defocusing and/or deformation being opposite to the defocusing and/or deformation caused by the eye to be examined whereby the OCT spot of the OCT illumination radiation is more sharply in focus and the OCT spot is more round in the eye than when the defocusing and/or the deformation is not applied to the OCT illumination radiation by the application of the adjustable collimation optical unit.

2. The microscope according to claim 1, wherein the wavefront measuring device measures spherical aberration of the eye to be examined.

3. The microscope according to claim 2, wherein the wavefront measuring device measures astigmatism of the eye to be examined.

4. The microscope according to claim 1, wherein the wavefront measuring device measures astigmatism of the eye to be examined.

5. The microscope according to claim 1, wherein the control unit actuates the collimation optical unit for the purposes of setting the beam diameter and/or the beam shape of the OCT spot.

6. The microscope according to claim 2, wherein the control unit actuates the collimation optical unit for the purposes of setting the beam diameter and/or the beam shape of the OCT spot.

7. The microscope according to claim 3, wherein the control unit actuates the collimation optical unit for the purposes of setting the beam diameter and/or the beam shape of the OCT spot.

8. The microscope according to claim 4, wherein the control unit actuates the collimation optical unit for the purposes of setting the beam diameter and/or the beam shape of the OCT spot.

9. The microscope according to claim 1, wherein the collimation optical unit comprises an axially displaceable lens, the axial position of which is set by operation of the control unit for purposes of setting the beam diameter of the OCT spot.

10. The microscope according to claim 6, wherein the collimation optical unit comprises an axially displaceable lens, the axial position of which is set by operation of the control unit for the purposes of setting the beam diameter of the OCT spot.

11. The microscope according to claim 5, wherein the collimation optical unit comprises a liquid lens, which is actuated by the control unit for purposes of setting the beam diameter and/or the beam shape of the OCT spot.

12. The microscope according to claim 9, wherein the collimation optical unit comprises a liquid lens, which is actuated by the control unit for purposes of setting the beam diameter and/or the beam shape of the OCT spot.

13. The microscope according to claim 5, wherein the collimation optical unit comprises an adaptive mirror, the control unit actuating said adaptive mirror for purposes of setting the beam diameter and/or the beam shape of the OCT spot.

14. The microscope according to claim 6, wherein the collimation optical unit comprises an adaptive mirror, the control unit actuating said adaptive mirror for purposes of setting the beam diameter and/or the beam shape of the OCT spot.

15. The microscope according to claim 9, wherein the collimation optical unit comprises an adaptive mirror, the control unit actuating said adaptive mirror for purposes of setting the beam diameter and/or the beam shape of the OCT spot.

16. The microscope according to claim 10, wherein the collimation optical unit comprises an adaptive mirror, the control unit actuating said adaptive mirror for purposes of setting the beam diameter and/or the beam shape of the OCT spot.

17. The microscope according to claim 11, wherein the collimation optical unit comprises an adaptive mirror, the control unit actuating said adaptive mirror for purposes of setting the beam diameter and/or the beam shape of the OCT spot.

18. The microscope according to claim 12, wherein the collimation optical unit comprises an adaptive mirror, the control unit actuating said adaptive mirror for purposes of setting the beam diameter and/or the beam shape of the OCT spot.

19. The microscope according to claim 1, wherein the observation beam path comprises a main objective.

20. The microscope according to claim 19, wherein the main objective is part of the OCT illumination beam path and/or part of a detection beam path of the wavefront measuring device.

* * * * *